(12) United States Patent
Player et al.

(10) Patent No.: US 7,429,603 B2
(45) Date of Patent: Sep. 30, 2008

(54) C-FMS KINASE INHIBITORS

(75) Inventors: Mark R. Player, Phoenixville, PA (US); Nand Baindur, Kendall Park, NJ (US); Benjamin Brandt, Highland Park, NJ (US); Naresh Chadha, Montville, NJ (US); Raymond J. Patch, Yardley, PA (US); Davoud Asgari, Plainsboro, NJ (US); Taxiarchis M. Georgiadis, Carmel, IN (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 486 days.

(21) Appl. No.: 10/831,216

(22) Filed: Apr. 26, 2004

(65) Prior Publication Data
US 2005/0004112 A1 Jan. 6, 2005

Related U.S. Application Data

(60) Provisional application No. 60/465,204, filed on Apr. 25, 2003.

(51) Int. Cl.
C07D 405/02 (2006.01)
A61K 31/445 (2006.01)

(52) U.S. Cl. .................. 514/326; 514/422; 546/214; 548/517

(58) Field of Classification Search .............. 549/487; 514/461, 326, 422; 546/214; 548/517
See application file for complete search history.

(56) References Cited

U.S. PATENT DOCUMENTS

| | | | |
|---|---|---|---|
| 3,717,579 A * | 2/1973 | Hofmann et al. ............ 514/352 |
| 3,862,152 A | 1/1975 | Kuwada et al. |
| 4,172,947 A | 10/1979 | Warner, Jr. et al. |
| 4,186,199 A | 1/1980 | Glamkowski et al. |
| 5,258,357 A | 11/1993 | Muenster et al. |
| 5,854,285 A * | 12/1998 | Sriram et al. ............... 514/514 |
| 6,380,247 B2 | 4/2002 | Konishi et al. |
| 6,420,567 B1 | 7/2002 | Wu et al. |
| 6,545,161 B2 | 4/2003 | Gupta et al. |
| 6,936,736 B2 | 8/2005 | Ikeda et al. |
| 7,012,094 B1 | 3/2006 | Bertenshaw et al. |
| 7,019,024 B2 | 3/2006 | Ognyanov et al. |
| 7,037,937 B2 | 5/2006 | Uckun et al. |
| 7,041,702 B1 | 5/2006 | Durant et al. |
| 7,045,551 B2 | 5/2006 | Wu et al. |
| 7,087,604 B2 | 8/2006 | Cherney |
| 7,098,240 B2 | 8/2006 | Griffiths et al. |
| 7,105,564 B1 | 9/2006 | Honma et al. |
| 7,109,243 B2 | 9/2006 | Liu et al. |
| 7,115,660 B2 | 10/2006 | Boger et al. |
| 7,179,840 B2 | 2/2007 | Rieck et al. |
| 2005/0004112 A1 | 1/2005 | Player et al. |
| 2005/0113566 A1 | 5/2005 | Player et al. |
| 2005/0131022 A1 | 6/2005 | Player et al. |

FOREIGN PATENT DOCUMENTS

| | | |
|---|---|---|
| DE | 26 35 818 A1 | 11/1977 |
| EP | 1 193 246 A1 | 4/2002 |
| GB | 1 508 947 | 4/1978 |
| WO | WO 95/19169 A2 | 7/1995 |
| WO | WO 02/28825 A | 4/2000 |
| WO | WO 00/27820 A | 5/2000 |
| WO | WO 00/62778 A1 | 10/2000 |
| WO | WO 02/068406 A | 9/2002 |
| WO | WO 03/103648 A1 | 12/2003 |
| WO | WO 03/103658 A1 | 12/2003 |
| WO | WO 2004/018461 A | 3/2004 |
| WO | WO 2004/022525 A | 3/2004 |
| WO | WO 2004/096795 A | 11/2004 |
| WO | WO 2006/047277 A2 | 5/2006 |
| WO | WO 2006/047504 A1 | 5/2006 |

OTHER PUBLICATIONS

CAS accerssion No. 1973:132353, Registry No. 41235-81-8.*

(Continued)

*Primary Examiner*—Zinna N. Davis

(57) ABSTRACT

The invention is directed to compounds of Formulae I, II and III:

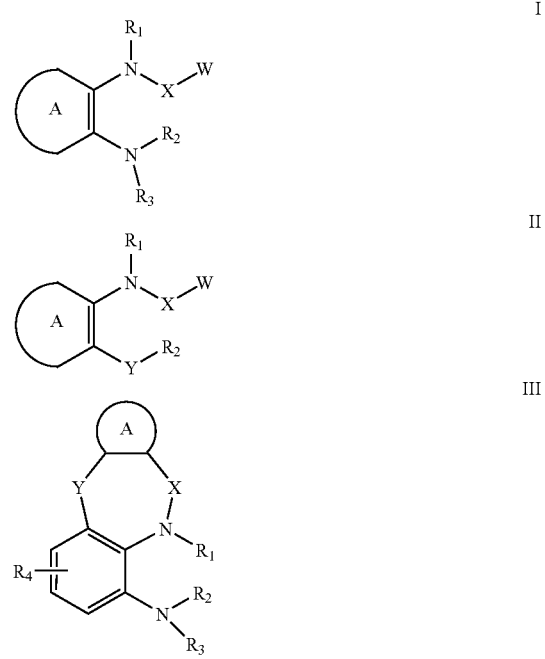

wherein A, $R_1$, $R_2$, $R_3$, $R_4$, X, Y and W are set forth in the specification, as well as solvates, hydrates, tautomers or pharmaceutically acceptable salts thereof, that inhibit protein tyrosine kinases, especially c-fms kinase.

2 Claims, No Drawings

OTHER PUBLICATIONS

Nilsson et al, J. Comb. Chem, vol. 3, pp. 546-553, 2001.*
Dhanoa et al, "Serine Proteases-Directed Small Molecule Probe Libraries", Medicinal Chemistry Research, vol. 8, No. 4/5 (1998) pp. 187-205 (XP009016618) ISSN: 1054-2523.
Database Beilstein, Beilstein Crossfire Institut Zur Foerderung Der Chemischen Wissenschaften, DE; BRN 214943, BRN 214944, BRN 303350 (XP002378023).
Blankley et al, "Antihypertensive Activity of 6-Arylpyrido[2,3-d]pyrimidin-7-amine Derivatives. 2. 7-Acyl Amide Analogues", Journal of Medicinal Chemistry, vol. 26, No. 3, Mar. 1, 1983, pp. 403-411, ISSN: 0022-2623 (XP002000852).
Chan et al, "Halogen Substitution at the Isoxazole Ring Enhances the Activity of N-(Isoxazolyl)sulfonamide Endothelin Antagonists", Bioorganic & Medicinal Chemistry Letters, vol. 6, No. 20, 1996, pp. 2393-2398, ISSN: 0960-894X (XP002314441).
Contreras et al, "Aminopyridazines as Acetylcholinesterase Inhibitors", Journal of Medicinal Chemistry, vol. 42, No. 4, Feb. 25, 1999, pp. 730-741, ISSN: 0022-2623 (XP002353008).
Moffett et al, "Antiulcer Agents. p-Aminobenzamido Aromatic Compounds", Journal of Medicinal Chemistry, vol. 14, No. 10, Oct. 1971, pp. 963-968, ISSN: 0022-2623 (XP002057311).
Robert-Piessard et al, "Non-acidic Anti-inflammatory Compounds: Activity of N-(4,6-dimethyl-2-pyridinyl) Benzamides and Derivatives", European Journal of Medicinal Chemistry, vol. 25, No. 1, 1990, pp. 9-19, ISSN: 0223-5234 (XP001062115).
Seydel et al, "Quantitative Structure-Pharmacokinetic Relationships Derived on Antibacterial Sulfonamides in Rats and Its Comparison to Quantitative Structure-Activity Relationships", Journal of Medicinal Chemistry, vol. 23, No. 6, Jun. 1980, pp. 607-613, ISSN: 0022-2623 (XP002392659).
Stein et al, "Discovery and Structure-Activity Relationships of Sulfonamide $Et_A$-Selective Antagonists", Journal of Medicinal Chemistry, vol. 38, No. 8, 1995, pp. 1344-1354, ISSN: 0022-2623 (XP002314442).
Database Beilstein, Beilstein Crossfire Institut Zur Foerderung Der Chemischen Wissenschaften, DE; BRN 316474 1954 (XP0023922714).
Database Beilstein, Beilstein Crossfire Institut Zur Foerderung Der Chemischen Wissenschaften, DE; BRN 393777 1966 (XP002392715).
Database Beilstein, Beilstein Crossfire Institut Zur Foerderung Der Chemischen Wissenschaften, DE; BRN 5344832 1922 (XP002392716).
Database Beilstein, Beilstein Crossfire Institut Zur Foerderung Der Chemischen Wissenschaften, DE; BRN 7604813 1996 (XP002392717).
Database Beilstein, Beilstein Crossfire Institut Zur Foerderung Der Chemischen Wissenschaften, DE; BRN 8848189 2001 (XP002392718).
Database Beilstein, Beilstein Crossfire Institut Zur Foerderung Der Chemischen Wissenschaften, DE; BRN 7600437 1996 (XP002392719).
Database Beilstein, Beilstein Crossfire Institut Zur Foerderung Der Chemischen Wissenschaften, DE; BRN 5448817 1991 (XP002392720).
Database Beilstein, Beilstein Crossfire Institut Zur Foerderung Der Chemischen Wissenschaften, DE; BRN 6975717 1985 (XP002392721).
Database Beilstein, Beilstein Crossfire Institut Zur Foerderung Der Chemischen Wissenschaften, DE; BRN 7036362 1994 (XP002392722).
Database Beilstein, Beilstein Crossfire Institut Zur Foerderung Der Chemischen Wissenschaften, DE; BRN 410569 1971 (XP002392723).
Database Beilstein, Beilstein Crossfire Institut Zur Foerderung Der Chemischen Wissenschaften, DE; BRN 438575 1973 (XP002392724).
Database Beilstein, Beilstein Crossfire Institut Zur Foerderung Der Chemischen Wissenschaften, DE; BRN622512 1974 (XP002392725).
Database Beilstein, Beilstein Crossfire Institut Zur Foerderung Der Chemischen Wissenschaften, DE; BRN4209696 1990 (XP00239276).
Database Beilstein, Beilstein Crossfire Institut Zur Foerderung Der Chemischen Wissenschaften, DE; BRN 309332 1946 (XP002392727).
Database Beilstein, Beilstein Crossfire Institut Zur Foerderung Der Chemischen Wissenschaften, DE; BRN 253307 1959 (XP002392728).
Database Beilstein, Beilstein Crossfire Institut Zur Foerderung Der Chemischen Wissenschaften, DE; BRN308560 1948 (XP002392729).
Database Chemcats, Chemical Abstracts Service, Columbus, Ohio, US; XP002307086, Order Nos. t0370-0639, t0369-0732. & "Ambinter Stock Screening Collection", Jan. 1, 2004, Ambinter, 46 Quai Loius Bleriot, F-75016 Paris, France.
WO 03/103648A (Muto et al; Inst of Medicinal Molecular) Dec. 18, 2003, Abstract; & Database Chemabs 'Online! Chemical Abstracts Service Columbus, Ohio, US; XP002307087, retrieved from STN Database accession No. 140:27850 Abstract; and RN's 439144-91-9, 634185-05-0, 634185-10-7, 634185-14-1.
WO 03/103658A (Muto et al; Inst of Medicinal Molecular) Dec. 18, 2003, Abstract; & Database Chemabs 'Online! Chemical Abstracts Service, Columbus, Ohio, US; XP002307891, retrieved from STN Database accession No. 140:42204 Abstract; and RN's 439144-91-9, 634185-05-0, 634185-10-7, 634185-14-1.
Database Chemcats, Chemical Abstracts Service, Columbus, Ohio, US; XP002307088, Order No. CHS2296111. & "ChemStar Product List" Apr. 24, 2003, Chemstar Ltd, Leningradskii Prospekt 47, Office 465, Moskow, 125167, Russia.
Database Beilstein, Beilstein Institute for Organic Chemistry, Frankfurt-Main, DE: XP002307089, Database Accession No. 290139 (BRN). & Chem. Ber., vol. 24, 1891, p. 2101.
Database Beilstein, Beilstein Institute for Organic Chemistry, Frankfurt-Main, DE; XP002307090, Database Accession Nos. 1012247, 1257241, 1319746, 1322924 (BRN's). & J. Chem. Soc., 1963, pp. 4666-4669.
Database Beilstein, Beilstein Institute for Organic Chemistry, Frankfurt-Main, DE; XP002307091, Database Accession Nos. 551856, 578613, 1257241, 1322924, 1324197 (BRN's). & J. Chem. Soc., 1964, p. 2609.
Database Beilstein, Beilstein Institute for Organic Chemistry, Frankfurt-Main, DE; XP002307092, Database Accession Nos. 1601543, 2983204, 2982987 (BRN's). & J. Chem. Soc. C, 1969, pp. 1444-1448.
Database Beilstein, Beilstein Institute for Organic Chemistry, Frankfurt-Main, DE; XP002307093, Database Accession Nos. 702242, 705174, 715898 (BRN's). & Justus Liebigs Ann. Chem., vol. 699, 1966, p. 88.
Database Beilstein, Beilstein Institute for Organic Chemistry, Frankfurt-Main, DE; XP002307094, Database Accession Nos. 126414, 1662045 (BRN's). & J. Chem. Soc. B, 1971, p. 696.
Database Beilstein, Beilstein Institute for Organic Chemistry, Frankfurt-Main, DE; XP002307095, Database Accession Nos. 5608933, 5609095 (BRN's). & Chem. Pharm. Bull., vol. 31, No. 9, 1983, pp. 3160-3167.
Database Beilstein, Beilstein Institute for Organic Chemistry, Frankfurt-Main, DE; XP002307096, Database Accession No. 5966001 (BRN). & Chem. Pharm. Bull., vol. 36, No. 9, 1988, pp. 3248-3252.
Melik-Organdzhanyan et al.: "New Method for the Synthesis of Polyfunctional 5-Aminopyrimidines", Chem. Heterocycl. Compd. Engl. Transl., 1983, pp. 100-102, XP009040286.
Yoshino et al: "Novel Sulfonamides as Potential, Systematically Active Antitumor Agents", J. Med. Chem., vol. 35, 1992, pp. 2496-2497, XP002307083.
Hodson et al.: "AlphaI-Adrenoceptor Activation: A Comparison of 4-(Anilinomethyl)imidazoles and 4-(Phenoxymethyl)imidazoles to Related 2-Imidazolines", Bioorg. Med. Chem. Lett., vol. 12, 2002, pp. 3449-3452, XP002307084.
Database Beilstein, Beilstein Institute for Organic Chemistry, Frankfurt-Main, DE; XP002307097, Database Accession Nos. 282633, 402265, 403511 (BRN's). & Helv. Chim. Acta, vol. 61, 1978, p. 2887.

Database Beilstein, Beilstein Institute for Organic Chemistry, Frankfurt-Main, DE; XP002307098, Database Accession Nos. 6972518, 6973696, 6974212, 6975313, 6975875 (BRN's). & Farmaco Ed. Sci., vol. 42, No. 3, 1987, pp. 231-236.

Database Beilstein, Beilstein Institute for Organic Chemistry, Frankfurt-Main, DE; XP002307099, Database Accession Nos. 1112966, 1378557, 1384830, 2732875, 2743259, 2743836, 2746021, 2752729, 2755871, 2774906 (BRN's). & Bull. Soc. Chim. Fr., 1973, pp. 3017-2018.

Database Beilstein, Beilstein Institute for Organic Chemistry, Frankfurt-Main, DE; XP002307100, Database Accession Nos. 4875002, 4878430, 4878634, 4880771, 4881664, 4884524 (BRN's). & J. Med. Chem., vol. 35, No. 5, 1992, pp. 804-807.

Database Beilstein, Beilstein Institute for Organic Chemistry, Frankfurt-Main, DE; XP002307101, Database Accession No. 177103 (BRN). & Arh. Chem., vol. 27, 1955, p. 33.

Database Beilstein, Beilstein Institute for Organic Chemistry, Frankfurt-Main, DE; XP002307102, Database Accession Nos. 28308, 252444 (BRN's). & Proc.-Indian Acad. Sci. Sect. A, vol. 38, 1953, p. 58.

Database Beilstein, Beilstein Institute for Organic Chemistry, Frankfurt-Main, DE; XP002307103, Database Accession Nos. 22169, 3751528 (BRN's). & J. Am. Chem. Soc., vol. 40, 1980, p. 566.

Database Beilstein, Beilstein Institute for Organic Chemistry, Frankfurt-Main, DE; XP002307104, Database Accession Nos. 197306, 3795001 (BRN's). & Gazz. Chim. Ital., vol. 80, 1950, p. 456.

Database Chemcats 'Online!, Chemical Abstracts Service, Columbus, Ohio, US; XP002307105, retrieved from STN, Order No. 2022-2088. & "Interchim Intermediates" Jul. 9, 2002, Interchim, 213 Avenue Kennedy, BP 1140, Montlucon, Cedex, 03103, France.

Klunder et al.: "Novel Non-Nucleoside Inhibitors of HIV-1 Reverse Transcriptase. 2. Tricyclic Pyridobenzoxazepinones and Dibenzoxazephinones.", J. Med. Chem., vol. 35, 1992, pp. 1887-1897, XP 002307085.

Traxler: "Tyrosine Kinase Inhibitors in Cancer Treatment (Part II)" Expert Opinion on Therapeutic Patents, Ashley Publications, GB, vol. 8, No. 12, 1998, pp. 1599-1625, XP001183544, ISSN: 1354-3776.

Showalter et al: "Tyrosine Kinase Inhibitors. 16. 6,5,6-Tricyclic Benzothieno [3,2-d]pyrimidines and Pyrimido[5,4-b]- and -[4,5-b]indoles as Potent Inhibitors of the Epidermal Growth Factor Receptor Tyrosine Kinase" Journal of Medicinal Chemistry, American Chemical Society. Washington, US, vol. 42, 1999, pp. 5464-5474, XP002210181, ISSN: 0022-2633.

International Search Report dated Dec. 9, 2004, for corresponding international application No. PCT/US2004/012729.

Database CA. Chemical Abstracts Service. Vostrova, L.N. 'Nitrogen Heterocycles Based on Derivatives of Diimidazo [1,5-a;1',5'-d]pyrazine-5,10-diones' Database Accession No. 1983:126026. XP002401298. Abstract Ukrainskii Khimicheskii Zhurnal (Russian Edition)(1982) 48(10)1074-7.

Database Chemcats. Chemical Abstracts Service. XP002401299. 'Enamine Screening Library' Jan. 24, 2006.

Dumas, J. 'Protein Kinase Inhibitors: Emerging Pharmacophores 1997-2000' Expert Opinion on Therapeutic Patents vol. 11 No. 3 pp. 405-429. XP002206851.

International Search Report re: PCT/US2005/038307 dated Oct. 19, 2006.

International Search Report re: PCT/US2006/014886 dated Nov. 2, 2006.

Beier et al, CA122:132943 (1995).

Freund et al, CA63:1170b (1982).

Snyder, Journal of Medicinal Chemistry (1967) 10(4):737-739.

* cited by examiner

C-FMS KINASE INHIBITORS

PRIORITY CLAIM

This application claims benefit under 35 U.S.C. § 119(e) to Provisional Application No. 60/465,204, filed Apr. 25, 2003.

FIELD OF THE INVENTION

The invention relates to novel compounds that function as protein tyrosine kinase inhibitors. More particularly, the invention relates to novel compounds that function as inhibitors of c-fms kinase.

BACKGROUND OF THE INVENTION

Protein kinases are enzymes that serve as key components of signal transduction pathways by catalyzing the transfer of the terminal phosphate from ATP to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. One embodiment of the invention is directed to the novel compounds of Formula I:

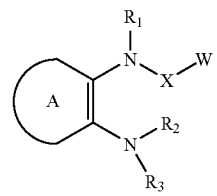

I or a solvate, hydrate, tautomer or pharmaceutically acceptable salt thereof, wherein A is
  phenyl, naphthyl or biphenyl, each of which may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —N($R_a$)$COR_b$, —$NO_2$, —$SO_2R_a$, —$SO_3R_a$ or —$SO_2NR_aR_b$; or
  a 5- to 7-membered mono- or a 8- to 10-membered bicyclic heteroaromatic ring having from one to four heteroatoms selected from N, O or S, and may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —N($R_a$)$COR_b$, —$NO_2$, —$SO_2R_a$, —$SO_3R_a$ or —$SO_2NR_aR_b$;

$R_1$ is
  —H, aryl, —$COR_a$, —$COR_a$, —$COOR_a$, —$CONR_aR_b$, —$SO_2R_a$ or —$SO_2NR_aR_b$;

X is
  —CO—, —C(=NH)—, —CS—, —CON($R_a$)—, —CS(N$R_a$)—, —$SO_2$— or —$CR_aR_b$—;

$R_2$ and $R_3$ are independently
—H, —$C_{1-6}$ alkyl, aryl, cycloalkyl, heterocyclyl, heteroaryl, —$COR_a$, —$COR_a$, —$COOR_a$, —$CONR_aR_b$, —$SO_2R_a$ or —$SO_2NR_aR_b$; or $R_2$ and $R_3$, taken together with the attached nitrogen, form a 5- to 7-membered heterocyclic or heteroaromatic ring containing from one to three heteroatoms selected from N, O or S, which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$; and W is
phenyl, naphthyl or biphenyl, each of which may be optionally substituted with one or more of $C_{1-4}$ alkyl, amino, aminoalkyl, hydroxyalkyl, alkoxyalkyl, halogen, hydroxy, —$CF_3$, alkoxy, aryloxy, arylalkoxy, —$OCF_3$, —$COR_a$, —CN, —$C(NH)NH_2$, —$COOR_a$, —$CONR_aR_b$, —$NHCOR_aR_b$, —$NHSO_2R_a$, —$NO_2$, —$SOR_a$, —$SO_3R_a$ or —$SO_2NR_aR_b$; or a 5- to 6-membered mono- or a 8- to 10-membered bicyclic heterocyclic or heteroaromatic ring having from one to four heteroatoms selected from N, O or S, and may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

In another embodiment, the invention is directed to the novel compounds of Formula II:

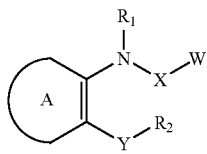

II or a solvate, hydrate, tautomer or pharmaceutically acceptable salt thereof, wherein A is
phenyl, naphthyl or biphenyl, each of which may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$; or a 5- to 7-membered mono- or a 8- to 10-membered bicyclic heteroaromatic ring having from one to four heteroatoms selected from N, O or S, and may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$C(NH)NH_2$, —$COOR_a$, —$CONR_aR_b$, —$N(R_a)$$COR_b$, —$NO_2$, —$SO_2R_a$, —$SO_3R_a$ or —$SO_2NR_aR_b$;

$R_1$ is
—H, aryl, —$COR_a$, —$COR_a$, —$COOR_a$, —$CONR_aR_b$, —$SO_2R_a$ or —$SO_2NR_aR_b$;

X is
—CO—, —C(=NH)—, —CS—, —CON($R_a$)—, CS(N$R_a$)—, —$SO_2$— or —C$R_aR_b$—;

Y is
—S—, —SO—, —$SO_2$—, —O— or direct link;

$R_2$ is
alkyl, cycloalkyl, heterocyclyl, aryl or heteroaryl, each of which may be optionally substituted with one or more halogens; and W is
phenyl, naphthyl or biphenyl, each of which may be optionally substituted with one or more of $C_{1-4}$ alkyl, amino, aminoalkyl, hydroxyalkyl, alkoxyalkyl, halogen, hydroxy, —$CF_3$, alkoxy, aryloxy, arylalkoxy, —$OCF_3$, —$COR_a$, —CN, —$C(NH)NH_2$, —$COOR_a$, —$CONR_aR_b$, —$NHCOR_aR_b$, —$NHSO_2R_a$, —$NO_2$, —$SOR_a$, —$SO_3R_a$ or —$SO_2NR_aR_b$; or a 5- to 6-membered mono- or a 8- to 10-membered bicyclic heterocyclic or heteroaromatic ring having from one to four heteroatoms selected from N, O or S, and may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Yet another embodiment of the invention is directed to the compounds of Formula III:

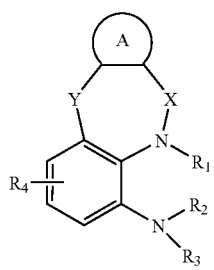

III or a solvate, hydrate, tautomer or pharmaceutically acceptable salt thereof, wherein A is
a 5- to 6-membered heteroaromatic ring having from one to four heteroatoms selected from N, O or S, and may be optionally substituted with —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —COR$_a$, —CN, —C(NH)NH$_2$, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$;

X is
—CO—, —C(=NH)—, —SO$_2$— or —CS—;

Y is
direct bond, —CH$_2$—, —CH$_2$CH$_2$—, —CH=CH—, —NR$_a$—, —O—, —S—, —SO—, —SO$_2$—, —CH$_2$O—, —OCH$_2$—, —NR$_a$CH$_2$—, —CH$_2$NR$_a$—, —CONR$_a$— or —NR$_a$CO—;

R$_1$ is
—H, aryl, —COR$_a$, —COR$_a$, —COOR$_a$, —CONR$_a$R$_b$, —SO$_2$R$_a$ or —SO$_2$NR$_a$R$_b$;

R$_2$ and R$_3$ are independently
—H, —C$_{1-6}$ alkyl, aryl, cycloalkyl, heterocyclyl, heteroaryl, —COR$_a$, —COR$_a$, —COOR$_a$, —CONR$_a$R$_b$, —SO$_2$R$_a$ or —SO$_2$NR$_a$R$_b$; or R$_2$ and R$_3$, taken together with the attached nitrogen, form
a 5- to 7-membered heterocyclic or heteroaromatic ring containing from one to three heteroatoms selected from N, O or S, which may be optionally substituted with —C$_{1-6}$ alkyl, amino, aminoalkyl, hydroxyalkyl, alkoxyalkyl, heteroaryl, halogen, hydroxy, —CF$_3$, alkoxy, aryl, aralkyl, heteroaralkyl, aryloxy, arylalkoxy, —OCF$_3$, —OCO-alkyl, —OCO-alkylamino, —OCO-alkylamido, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$, and R$_4$ is
one or more of —H, —C$_{1-6}$ alkyl, amino, aminoalkyl, hydroxyalkyl, alkoxyalkyl, sulfonamidoalkyl, guanidinoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$, wherein R$_a$ and R$_b$ are independently hydrogen, alkyl, cycloalkyl, haloalkyl, aryl, aralkyl, heteroaralkyl or heteroaryl.

The compounds of Formulae I and II are especially potent inhibitors of the c-fms protein tyrosine kinase. The compounds of Formula III are expected to exhibit similar inhibitory potencies.

The invention also relates to methods of inhibiting protein tyrosine kinase activity in a mammal by administration of a therapeutically effective amount of at least one compound of Formula I, II or III.

DETAILED DESCRIPTION OF THE INVENTION

The invention is directed to the novel compounds of Formula I:

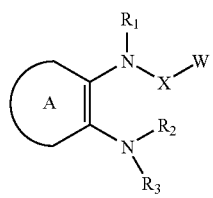

I or a solvate, hydrate, tautomer or pharmaceutically acceptable salt thereof, wherein A is
phenyl, naphthyl or biphenyl, each of which may be optionally substituted with one or more of —C$_{1-6}$ alkyl, amino, aminoalkyl, hydroxyalkyl, alkoxyalkyl, sulfonamidoalkyl, guanidinoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —C(NH)NH$_2$, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$; or a 5- to 7-membered mono- or a 8- to 10-membered bicyclic heteroaromatic ring having from one to four heteroatoms selected from N, O or S, and may be optionally substituted with one or more of —C$_{1-6}$ alkyl, amino, aminoalkyl, hydroxyalkyl, alkoxyalkyl, sulfonamidoalkyl, guanidinoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —C(NH)NH$_2$, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$;

R$_1$ is
—H, aryl, —COR$_a$, —COR$_a$, —COOR$_a$, —CONR$_a$R$_b$, —SO$_2$R$_a$ or —SO$_2$NR$_a$R$_b$;

X is
—CO—, —C(=NH)—, —CS—, —CON(R$_a$)—, —CS(NR$_a$)—, —SO$_2$— or —CR$_a$R$_b$—;

R$_2$ and R$_3$ are independently
—H, —C$_{1-6}$ alkyl, aryl, cycloalkyl, heterocyclyl, heteroaryl, —COR$_a$, —COR$_a$, —COOR$_a$, —CONR$_a$R$_b$, —SO$_2$R$_a$ or —SO$_2$NR$_a$R$_b$; or R$_2$ and R$_3$, taken together with the attached nitrogen, form
a 5- to 7-membered heterocyclic or heteroaromatic ring containing from one to three heteroatoms selected from N, O or S, which may be optionally substituted with —C$_{1-6}$ alkyl, amino, aminoalkyl, hydroxyalkyl, alkoxyalkyl, heteroaryl, halogen, hydroxy, —CF$_3$, alkoxy, aryl, aralkyl, heteroaralkyl, aryloxy, arylalkoxy, —OCF$_3$, —OCO-alkyl, —OCO-alkylamino, —OCO-alkylamido, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$; and W is
phenyl, naphthyl or biphenyl, each of which may be optionally substituted with one or more of C$_{1-4}$ alkyl, amino, aminoalkyl, hydroxyalkyl, alkoxyalkyl, halogen, hydroxy, —CF$_3$, alkoxy, aryloxy, arylalkoxy, —OCF$_3$, —COR$_a$, —CN, —C(NH)NH$_2$, —COOR$_a$, —CONR$_a$R$_b$, —NHCOR$_b$, —NHSO$_2$R$_a$, —NO$_2$, —SOR$_a$, —SO$_3$R$_a$ or —SO$_2$NR$_a$R$_b$; or a 5- to 6-membered mono- or a 8- to 10-membered bicyclic heterocyclic or heteroaromatic ring having from one to four heteroatoms selected from N, O or S, and may be optionally substituted with —C$_{1-6}$ alkyl, amino, aminoalkyl, hydroxyalkyl, alkoxyalkyl, heteroaryl, halogen, hydroxy, —CF$_3$, alkoxy, aryl, aralkyl, heteroaralkyl, aryloxy, arylalkoxy, —OCF$_3$, —OCO-alkyl, —OCO-alkylamino, —OCO-alkylamido, —COR$_a$, —CN, —C(NH)NH$_2$, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$, wherein R$_a$ and R$_b$ are independently hydrogen, alkyl, cycloalkyl, haloalkyl, aryl, aralkyl, heteroaralkyl or heteroaryl.

In another embodiment, the invention is directed to the novel compounds of Formula II:

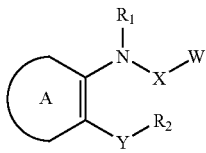

II or a solvate, hydrate, tautomer or pharmaceutically acceptable salt thereof, wherein A is
  phenyl, naphthyl or biphenyl, each of which may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$; or
  a 5- to 7-membered mono- or a 8- to 10-membered bicyclic heteroaromatic ring having from one to four heteroatoms selected from N, O or S, and may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$;

$R_1$ is
  —H, aryl, —$COR_a$, —$COR_a$, —$COOR_a$, —$CONR_aR_b$, —$SO_2R_a$ or —$SO_2NR_aR_b$;

X is
  —CO—, —C(=NH)—, —CS—, —$CON(R_a)$—, —$CS(NR_a)$—, —$SO_2$— or —$CR_aR_b$—;

Y is
  —S—, —SO—, —$SO_2$—, —O— or direct link;

$R_2$ is
  alkyl, cycloalkyl, heterocyclyl, aryl or heteroaryl, each of which may be optionally substituted with one or more halogens; and W is
  phenyl, naphthyl or biphenyl, each of which may be optionally substituted with one or more of $C_{1-4}$ alkyl, amino, aminoalkyl, hydroxyalkyl, alkoxyalkyl, halogen, hydroxy, —$CF_3$, alkoxy, aryloxy, arylalkoxy, —$OCF_3$, —$COR_a$, —CN, —$C(NH)NH_2$, —$COOR_a$, —$CONR_aR_b$, —$NHCOR_aR_b$, —$NHSO_2R_a$, —$NO_2$, —$SOR_a$, —$SO_3R_a$ or —$SO_2NR_aR_b$; or
  a 5- to 6-membered mono- or a 8- to 10-membered bicyclic heterocyclic or heteroaromatic ring having from one to four heteroatoms selected from N, O or S, and may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Yet another embodiment of the invention is directed to the compounds of Formula III:

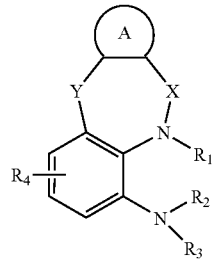

III or a solvate, hydrate, tautomer or pharmaceutically acceptable salt thereof, wherein A is
  a 5- to 6-membered heteroaromatic ring having from one to four heteroatoms selected from N, O or S, and may be optionally substituted with —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$;

X is
  —CO—, —C(=NH)—, —$SO_2$— or —CS—;

Y is
  direct bond, —$CH_2$—, —$CH_2CH_2$—, —CH=CH—, —$NR_a$—, —O—, —S—, —SO—, —$SO_2$—, —$CH_2O$—, —$OCH_2$—, —$NR_aCH_2$—, —$CH_2NR_a$—, —$CONR_a$— or —$NR_aCO$—;

$R_1$ is
  —H, aryl, —$COR_a$, —$COR_a$, —$COOR_a$, —$CONR_aR_b$, —$SO_2R_a$ or —$SO_2NR_aR_b$;

$R_2$ and $R_3$ are independently
  —H, —$C_{1-6}$ alkyl, aryl, cycloalkyl, heterocyclyl, heteroaryl, —$COR_a$, —$COR_a$, —$COOR_a$, —$CONR_aR_b$, —$SO_2R_a$ or —$SO_2NR_aR_b$; or $R_2$ and $R_3$, taken together with the attached nitrogen, form
  a 5- to 7-membered heterocyclic or heteroaromatic ring containing from one to three heteroatoms selected from N, O or S, which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, and $R_4$ is
  one or more of —H, —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Preferred compounds of Formula I are those wherein
A is phenyl;
$R_1$ is —H; and
$R_2$ and $R_3$, taken together with the attached nitrogen, form a piperidine, piperazine, morpholine, thiomorpholine, pyrrolidine, pyrroline, pyrazolidine, pyrazoline, imidazolidine or imidazoline ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Particularly preferred compounds of Formula I are those wherein
A is phenyl;
$R_1$ is —H;
$R_2$ and $R_3$, taken together with the attached nitrogen, form a piperidine, piperazine, morpholine, thiomorpholine, pyrrolidine, pyrroline, pyrazolidine, pyrazoline, imidazolidine or imidazoline ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$; and
W is a phenyl, furan, thiophene, isoxazole, pyrrole, oxazole, thiazole, imidazole, pyrazole, isothiazole, triazole, pyridine, pyridazine, pyrimidine, pyrazine or triazine ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Preferred compounds of Formula II are those wherein
A is phenyl;
$R_1$ is —H; and
W is a phenyl, furan, thiophene, isoxazole, pyrrole, oxazole, thiazole, imidazole, pyrazole, isothiazole, triazole, pyridine, pyridazine, pyrimidine, pyrazine or triazine ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$,
wherein $R_a$ and $R_b$ are independently hydrogen, alkyl, cycloalkyl, haloalkyl, aryl, aralkyl, heteroaralkyl or heteroaryl.

It is expected that the preferred compounds of Formula III will have similar or identical $R_2$ and $R_3$ substituents as compared to the preferred compounds of Formulae I and II.

The most preferred compounds of Formula I include, but are not limited to, 5-nitro-furan-2-carboxylic acid (2-piperidin-1-yl-phenyl)-amide; isoxazole-5-carboxylic acid (2-piperidin-1-yl-phenyl)-amide 5-nitro-furan-2-carboxylic acid (5-hydroxymethyl-2-piperidin-1-yl-phenyl)-amide; 5-nitro-furan-2-carboxylic acid [2-(3-methyl-piperidin-1-yl)-phenyl]-amide; 4-nitro-pyridine-2-carboxylic acid (2-piperidin-1-yl-phenyl)-amide; 5-nitro-furan-2-carboxylic acid (2-morpholin-4-yl-phenyl)-amide; 5-chloro-furan-2-carboxylic acid (2-piperidin-1-yl-phenyl)-amide; 5-nitro-furan-2-carboxylic acid [2-(trans-2,6-dimethyl-morpholin-4-yl)-phenyl]-amide; 3-nitro-N-(2-piperidin-1-yl-phenyl)-benzamide; 5-bromo-furan-2-carboxylic acid (2-piperidin-1-yl-phenyl)-amide; 5-acetyl-thiophene-2-carboxylic acid (2-piperidin-1-yl-phenyl)-amide; 5-nitro-furan-2-carboxylic acid [2-(cis-2,6-dimethyl-morpholin-4-yl)-phenyl]-amide; 4-nitro-2H-pyrazole-3-carboxylic acid (2-piperidin-1-yl-phenyl)-amide; 5-formyl-furan-2-carboxylic acid (2-piperidin-1-yl-phenyl)-amide; 5-(2-piperidin-1-yl-phenylcarbamoyl)-furan-2-carboxylic acid; isoxazole-5-carboxylic acid (2-morpholin-4-yl-phenyl)-amide; 5-cyano-furan-2-carboxylic acid (2-piperidin-1-yl-phenyl)-amide; 5-nitro-furan-2-carboxylic acid [2-(4-methyl-piperidin-1-yl)-phenyl]-amide; 5-nitro-furan-2-carboxylic acid [2-(4-methyl-piperazin-1-yl)-phenyl]-amide; 5-nitro-furan-2-carboxylic acid [2-(4-hydroxy-piperidin-1-yl)-phenyl]-amide; 5-nitro-furan-2-carboxylic acid [2-(4-hydroxymethyl-piperidin-1-yl)-phenyl]-amide; 5-nitro-furan-2-carboxylic acid (2-azepan-1-yl-phenyl)-amide; 5-cyano-furan-2-carboxylic acid (5-hydroxymethyl-2-piperidin-1-yl-phenyl)-amide; 5-cyano-furan 2-carboxylic acid [2-(4-methyl-piperidin-1-yl)-phenyl]-amide; 5-cyano-furan-2-carboxylic acid [2-(4-hydroxymethyl-piperidin-1-yl)-phenyl]-amide; 5-cyano-furan-2-carboxylic acid {2-[4-(2-hydroxy-ethyl)-piperidin-1-yl]-phenyl}-amide; 5-cyano-furan-2-carboxylic acid [5-hydroxymethyl-2-(4-methyl-piperidin-1-yl)-phenyl]-amide; 5-cyano-furan-2-carboxylic acid [5-hydroxymethyl-2-(4-hydroxymethyl-piperidin-1-yl)-phenyl]-amide; 5-cyano-furan-2-carboxylic acid [2-(4-ethyl-piperidin-1-yl)-5-hydroxymethyl-phenyl]-amide; 5-cyano-furan-2-carboxylic acid {2-[4-(2-hydroxy-ethyl)-piperidin-1-yl]-5-hydroxymethyl-phenyl}-amide; 5-cyano-furan-2-carboxylic acid [2-(4-ethyl-piperidin-1-yl)-phenyl]-amide; 4-nitro-1H-pyrrole-2-carboxylic acid [2-(4-ethyl-piperidin-1-yl)-phenyl]-amide; 4-nitro-1H-pyrrole-2-carboxylic acid [2-(4-methyl-piperidin-1-yl)-phenyl]-amide; 4-nitro-1H-pyrrole-2-carboxylic acid [5-hydroxymethyl-2-(4-methyl-piperidin-1-yl)-phenyl]-amide; 4-nitro-1H-pyrrole-2-carboxylic acid [5-hydroxymethyl-2-(4-ethyl-piperidin-1-yl)-phenyl]-amide; 4-nitro-1H-pyrrole-2-carboxylic acid {2-[4-(2-hydroxy-ethyl)-piperidin-1-yl]-5-hydroxymethyl-phenyl}-amide; 4-cyano-1H-pyrrole-2-carboxylic acid (2-piperidin-1-yl-phenyl)-amide; 4-cyano-1H-pyrrole-2-carboxylic acid [2-(4-ethyl-piperidin-1-yl)-phenyl]-amide; 4-cyano-1H-pyrrole-2-carboxylic acid [2-(4-methyl-piperidin-1-yl)-phenyl]-amide; 4-cyano-1H-pyrrole-2-carboxylic acid [5-hydroxymethyl-2-(4-methyl-piperidin-1-yl)-phenyl]-amide; 4-cyano-1H-pyrrole-2-carboxylic acid [5-hydroxymethyl-2-(4-ethyl-piperidin-1-yl)-phenyl]-amide; 4-cyano-1H-pyrrole-2-carboxylic acid {2-[4-(2-hydroxy-ethyl)-piperidin-1-yl]-5-hydroxymethyl-phenyl}-amide; 5-cyano-furan-2-carboxylic acid (5-methylsulfonamidomethyl-2-piperidin-1-yl-phenyl)-amide; 5-cyano-furan-2-carboxylic acid (5-guanidinomethyl-2-piperidin-1-yl-phenyl)-amide; 5-cyano-furan-2-carboxylic acid [5-(4-methyl-piperazin-1-ylmethyl)-2-piperidin-1-yl-phenyl]-amide; 5-cyano-furan-2-carboxylic acid (4-fluoro-2-piperidin-1-yl-phenyl)-amide; 5-cyano-furan-2-carboxylic acid (4-chloro-2-piperidin-1-yl-phenyl)-amide; 5-cyano-furan-2-carboxylic acid (5-cyano-2-piperidin-1-yl-phenyl)-amide; 5-cyano-furan-2-carboxylic acid {5-[(2,3-dihydroxy-propylamino)-methyl]-2-piperidin-1-yl-phenyl}-amide; 5-nitro-2H-pyrazole-3-carboxylic acid (2-piperidin-1-yl-phenyl)-amide and pharmaceutically acceptable salts thereof.

The most preferred compounds of Formula II include 5-nitro-furan-2-carboxylic acid [2-(2-chloro-1,1,2-trifluoro-ethylsulfanyl)-phenyl]-amide; 5-nitro-furan-2-carboxylic acid (2-ethoxyphenyl)-amide and pharmaceutically acceptable salts thereof.

The invention also relates to methods of inhibiting protein tyrosine kinase activity in a mammal by administration of a therapeutically effective amount of at least one compound of Formula I, II or III. A preferred tyrosine kinase is c-fms.

The invention is considered to include the enantiomeric, diastereomeric and tautomeric forms of all compounds of Formulae I, II and III as well as their racemic mixtures. In addition, some of the compounds represented by Formulae I, II and III may be prodrugs, i.e., derivatives of an acting drug that possess superior delivery capabilities and therapeutic value as compared to the acting drug. Prodrugs are transformed into active drugs by in vivo enzymatic or chemical processes.

1. Definitions

The term "alkyl" refers to both linear and branched chain radicals of up to 12 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "cycloalkyl" refers to a saturated or partially unsaturated ring composed of from 3 to 8 carbon atoms. Alkyl substituents may optionally be present on the ring. Examples include cyclopropyl, 1,1-dimethyl cyclobutyl, 1,2,3-trimethylcyclopentyl, cyclohexyl and cyclohexenyl.

The term "heterocyclyl" refers to a nonaromatic (i.e. saturated or partially unsaturated) ring composed of from 3 to 7 carbon atoms and at least one heteroatom selected from N, O or S. Alkyl substituents may optionally be present on the ring. Examples include tetrahydrofuryl, dihydropyranyl, piperidyl, 2,5-dimethypiperidyl, morpholinyl, piperazinyl, thiomorpholinyl, pyrrolidinyl, pyrrolinyl, pyrazolidinyl, pyrazolinyl, imidazolidinyl and imidazolinyl.

The term "heterocyclylalkyl" refers to a $C_{1-6}$ alkyl group containing a heterocyclyl substituent. Examples include dihydropyranylethyl and 2-morpholinylpropyl.

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain.

The term "alkoxyalkyl" refers to at least one alkoxy group bonded to any carbon atom along an alkyl chain.

The term "polyalkoxyalkyl" refers to long-chain alkoxy compounds and includes polyethylene glycols of discreet or monodispersed sizes.

The term "thioalkyl" refers to at least one sulfur group bonded to any carbon atom along an alkyl chain. The sulfur group may be at any oxidation state and includes sulfoxides, sulfones and sulfates.

The term "carboxyalkyl" refers to at least one carboxylate group bonded to any carbon atom along an alkyl chain. The term "carboxylate group" includes carboxylic acids and alkyl, cycloalkyl, aryl or aralkyl carboxylate esters.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroaralkyl" refers to a $C_{1-6}$ alkyl group having a heteroaryl substituent. Examples include furylethyl and 2-quinolinylpropyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napththalene.

The term "aralkyl" refers to a $C_{1-6}$ alkyl group containing an aryl substituent. Examples include benzyl, phenylethyl or 2-naphthylmethyl.

The term "heteroaralkyl" refers to a $C_{1-6}$ alkyl group containing a heteroaryl substituent. Examples include furylmethyl and pyridylpropyl.

The term "aryloxy" refers to an oxygen atom bound to an aryl substituent. Examples include phenoxy and benzyloxy.

The term "arylalkoxy" refers to an alkoxy group bound to an aryl substituent. Examples include phenylmethyl ether.

The term "acyl" refers to the group —C(O)$R_a$, where $R_a$ is alkyl, aryl, aralkyl, heteroaryl and heteroaralkyl. An "acylating agent" adds the —C(O)$R_a$ group to a molecule.

The term "sulfonyl" refers to the group —S(O)$_2 R_a$, where $R_a$ is hydrogen, alkyl, cycloalkyl, haloalkyl, aryl, aralkyl, heteroaryl and heteroaralkyl. A "sulfonylating agent" adds the —S(O)$_2 R_a$ group to a molecule.

II. Therapeutic Uses

The compounds of Formulae I, II and III represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I, II or III. A preferred tyrosine kinase is c-fms. In one embodiment of inhibiting a protein tyrosine kinase, at least one of the compounds of Formula I, II or III is combined with a known tyrosine kinase inhibitor.

In various embodiments of the invention, the protein tyrosine kinases inhibited by the compounds of Formulae I, II and III are located in cells, in a mammal or in vitro. In the case of mammals, which includes humans, a therapeutically effective amount of a pharmaceutically acceptable form of at least one of the compounds of Formula I, II or III is administered.

The invention further provides methods of treating cancer in mammals, including humans, by administration of a therapeutically effective amount of a pharmaceutically acceptable composition of least one compound of Formula I, II or III. Exemplary cancers include, but are not limited to, breast cancer, colon cancer, stomach cancer, hairy cell leukemia and non-small lung carcinoma. In one embodiment of the invention, an effective amount of at least one compound of Formula I, II or III is administered in combination with an effective amount of a chemotherapeutic agent.

The invention also provides methods of treating cardiovascular and inflammatory diseases in mammals, including humans, by administration of a therapeutically effective amount of a pharmaceutically acceptable form of at least one of the compounds of Formula I, II or III. Example of diseases that may be effectively treated include glomerulonephritis, rheumatoid arthritis, psoriasis, diabetes, tumor related angiogenesis, restenosis, schizophrenia and Alzheimer's dementia.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

The compounds of Formulae I, II and III may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formulae I, II and III include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

III. Methods of Preparation

The compounds of Formulae I, II and III may be prepared by either solid phase support methodology or by solution-phase synthesis. Exemplary synthetic routes for generating amides of the invention are described below.

EXAMPLE 1

General Procedure for Preparation of Amides

5-Nitro-furan-2-carboxylic acid phenylamides

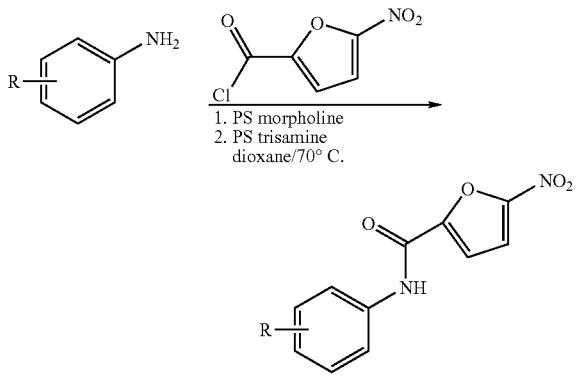

A solution of aniline (10 mg, 0.069 mmol) in dioxane (0.5 mL) was treated with polystyrene ("PS") morpholine resin (Aldrich) (50 mg, 0.14 mmol), followed by the addition of a solution of 5-nitro-furan-2-carbonyl chloride (Lancaster) (15 mg, 0.086 mmol) in dioxane (0.5 mL). The reaction was heated to 70° C. and agitated for 2 h. The reaction was treated with PS trisamine (Aldrich) (25 mg, 0.12 mmol) and heated to 70° C. for an additional 2 h. Filtration gave the desired product in >80% yield.

EXAMPLE 2

Procedure 2 for Preparation of Amides

Isoxazole-5-carboxylic acid
(2-piperidin-1-yl-phenyl)-amide

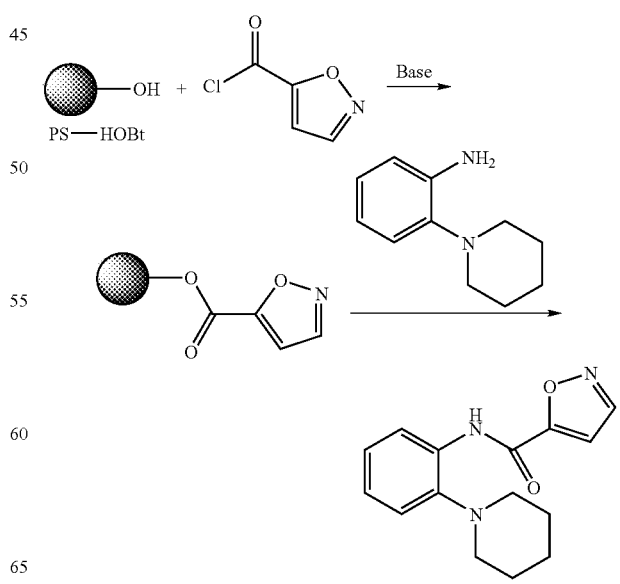

To PS-HOBt resin (0.1 mmol) was added anhydrous dichloromethane ("DCM") (1 mL) followed by pyridine (0.5 mmol) and isoxazole-5-carbonyl chloride (Lancaster) (0.3 mmol). The mixture was shaken at room temperature for 3 h and was then filtered. The resin was washed successively with tetrahydrofuran ("THF") (3×) and DCM (3×) and dried in vacuo. To this acylated resin was added a solution of 2-piperidinoaniline (Lancaster) (0.05 mmol, 0.5 eq) in anhydrous THF (1 mL) and the mixture was shaken at room temperature for 16 h. The mixtue was then filtered and the resin washed with THF and DCM as described above. The combined filtrate and washings were concentrated under reduced pressure to yield the product. Yield: 100%. MS: 272 (M+1). LC/MS purity: 100%. $^1$HNMR (CDCl$_3$, 300 MHz): δ 8.2 (d, 1H), 7.85 (t, 2H), 7.55 (m, 1H), 7.4 (m, 2H), 3.8-3.2 (bm, 4H), 2.7-1.9 (bm, 4H).

EXAMPLE 2-A

5-Nitro-furan-2-carboxylic acid (2-piperidin-1-yl-phenyl)-amide

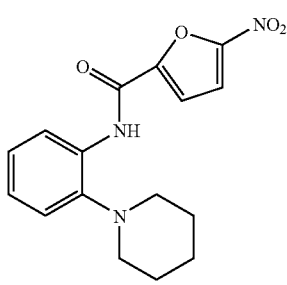

The compound was prepared according to the procedure described in Example 2 from 5-nitro-furan-2-carbonyl chloride and 2-piperidinoaniline. Yield: 100%. MS: 316 (M+1). LC/MS purity: 100%. $^1$HNMR (CDCl$_3$, 300 MHz): δ 8.2 (d, 1H), 7.85 (d, 1H), 7.55 (m, 1H), 7.4 (m, 3H), 3.8-3.2 (bm, 4H), 2.7-1.9 (bm, 6H).

EXAMPLE 3

Procedure 3 for Preparation of Amides

5-Nitro-thiophene-2-carboxylic acid (2-piperidin-1-yl-phenyl))-amide

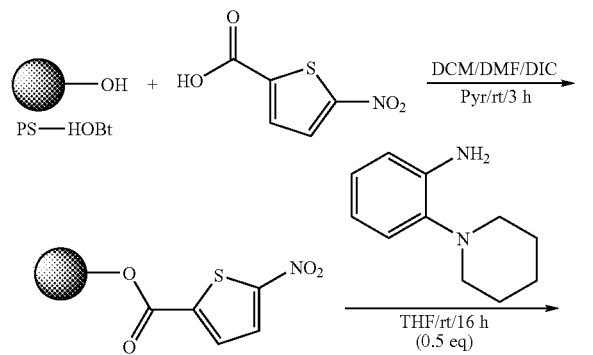

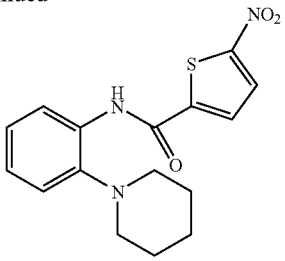

To PS-HOBt resin (0.15 mmol) was added 2 mL of a solution of pyridine (0.09 mmol) in DCM and 0.6 mL of a solution of the carboxylic acid (0.23 mmol) in N,N-dimethyl formamide ("DMF"). The mixture was shaken at room temperature for 5 min before the addition of 0.4 mL of a solution of 1,3-diisopropylcarbodiimide ("DIC") (0.66 mmol) in DCM. The mixture was shaken at room temperature for 3 h and filtered. The resin was washed with DMF (3×), THF (3×) and DCM (3×) and dried in vacuo. To this acyl resin was added a solution of 2-piperidinoaniline (0.075 mmol; 0.5 eq) in anhydrous THF (1 mL) and the mixture was shaken at room temperature for 16 h. The reaction was then filtered and the resin washed with THF and DCM. The combined filtrate and washings were concentrated in vacuo to yield the product. MS: 332 (M+1). LC/MS: 100% purity. $^1$H NMR (CDCl$_3$, 300 MHz): δ 7.95 (d, 2H), 7.5 (m, 2H), 7.2 (m, 2H), 2.85 (m, 4H), 1.8-1.6 (bm, 4H), 1.5 (bm, 2H).

EXAMPLE 4

Procedure 4 for Preparation of Amides

5-Bromo-furan-2-carboxylic acid (2-piperidin-1-yl-phenyl)-amide

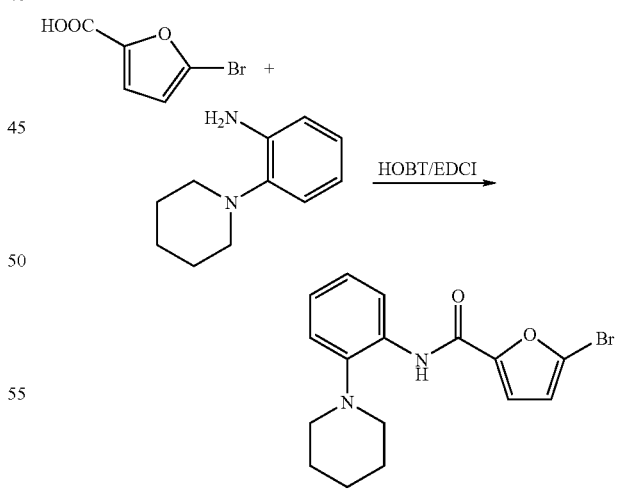

A solution of 5-bromofuroic acid (Aldrich) (1.0 mmol), 2-piperdinoaniline (1.0 mmol), 1-hydroxybenzotriazole hydrate ("HOBT") (1.2 mmol), and triethylamine ("Et$_3$N") (2 mmol) in DCM (10 mL) was stirred for 10 min at room temperature. 1-(3-Dimethylaminopropyl)-3-ethylcarbodiimide hydrochloride ("EDCI") (1.2 mmol) was then added and the resulting orange solution was stirred overnight. The reaction mixture was treated with saturated sodium bicarbonate ("NaHCO₃") solution (10 mL) and extracted with DCM. The combined organic layers were dried over MgSO₄, and concentrated under reduced pressure to afford the crude product as an orange solid. Purification by silica gel chromatography afforded the pure yellow product in 85% yield. MS: 349 (M+1). ¹H NMR (CDCl₃, 300 MHz): δ 9.75 (br s, 1H), 8.45 (d, 1H), 7.22-7.05 (m, 4H), 6.50 (d, 1H), 3.00-2.80 (m, 4H), 1.95-1.80 (m, 4H), 1.75-1.60 (m, 2H).

EXAMPLE 4-A 5-(2-Piperidin-1-yl-phenylcarbamoyl)-furan-2-carboxylic acid

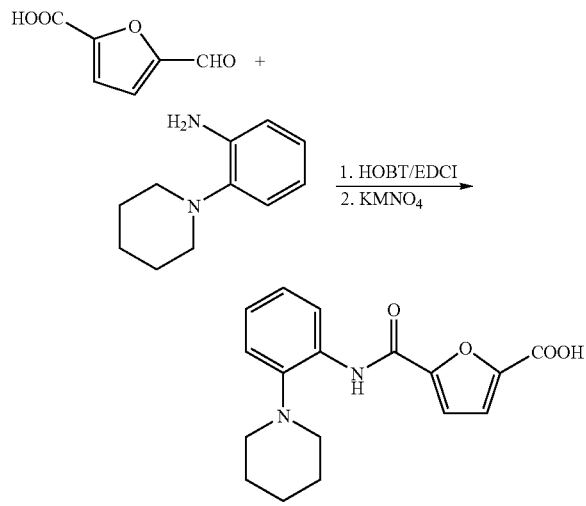

A solution of 5-formyl-2-furancarboxylic acid (TCI) (1.0 mmol), 2-piperidinoaniline (1.0 mmol), HOBT (1.2 mmol), and Et₃N (2 mmol) in DCM (10 mL) was stirred for 10 min at room temperature. EDCI (1.2 mmol) was then added and the resulting orange solution was stirred overnight. The reaction mixture was treated with saturated NaHCO₃ solution (10 mL) and extracted with DCM. The combined organic layers were dried over MgSO₄, and concentrated under reduced pressure to afford the crude product as an orange solid. Purification by silica gel chromatography afforded the amidoaldehyde product in 80% yield. The aldehyde product (1 mmol) was dissolved in H₂O/dimethoxyethane ("DME") (2:1, 5 mL) containing sodium carbonate ("Na₂CO₃") (2 mol). In a separate flask, potassium permanganate ("KMnO₄") (1.3 mmol) was dissolved in H₂O (5 mL) and was slowly added to the reaction flask at 45° C. The reaction was stirred overnight at room temperature, filtered through a plug of celite, and then acidified to a pH of 3 to 4 using a hydrochloric acid ("HCl") solution (1 N). The product, which precipitated out as a white solid, was filtered, washed with H₂O and dried under high vacuum to afford pure product. MS: 315 (M+1). ¹H NMR (DMSO-d₆, 300 MHz): δ 13.60 (br s, 1H), 9.90 (s, 1H), 8.25 (dd, 1H), 7.36 (dd, 2H), 7.35-7.25 (m, 1H), 7.20-7.10 (m, 2H), 2.85-2.65 (m, 4H), 1.85-1.65 (m, 4H), 1.65-1.45 (m, 2H).

EXAMPLE 5

Procedure for Preparation of Reduced Amides 5-(Nitro-furan-2-ylmethyl)-(2-piperidin-1-yl-phenyl)-amine

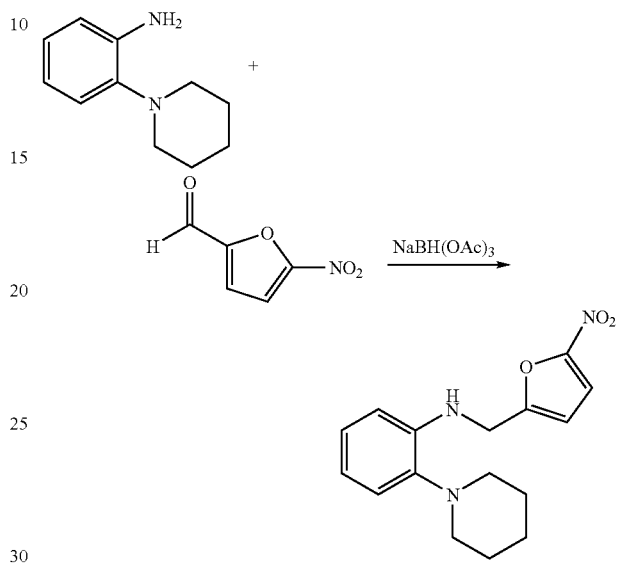

A solution of 2-piperidinoaniline (1 mmol), 5-nitro-furan-2-carbaldehyde (1.1 mmol) and sodium triacetoxyborohydride ("NaBH(OAc)₃") (2 mmol) in anhydrous DCM (10 mL) was stirred 16 h at room temperature. The mixture was then washed successively with water, dilute aqueous sodium hydroxide ("NaOH"), water and brine before being dried over MgSO₄, filtered and concentrated under reduced pressure. Purification of the residual oil by flash silica gel chromatography yielded the product. MS: 301 (M+1). LC/MS purity: 100%. ¹H NMR (CDCl₃, 300 MHz): δ 7.25 (d, 1H), 7.15-6.95 (m, 2H), 6.75 (t, 1H), 6.55 (d, 1H), 5.4 (bs, 1H), 4.45 (s, 2H), 2.8 (bm, 4H), 1.8-1.5 (bm, 6H).

EXAMPLE 6

Preparation of 5-Cyano-furan-2-carboxylic acid [5-hydroxymethyl-2-(4-methyl-piperidin-1-yl)-phenyl]-amide A. 2-Cyano-5-furancarboxylic acid

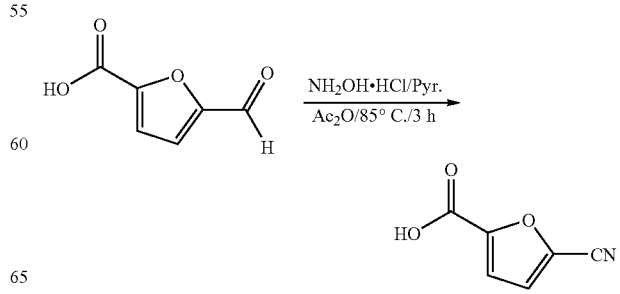

To a solution of 2-fornyl-5-furancarboxylic acid (0.28 g, 2.0 mol) in pyridine (5.0 mL) was added hydroxylamine hydrochloride ("NH$_2$OH.HCl") (0.27 g, 4.0 mol). The mixture was heated to 85° C. before the addition of acetic anhydride (4.0 ml). The reaction mixture was stirred at 85° C. for 3 h, cooled to 60° C. and poured into water (25 mL). The mixture was cooled to room temperature and stirred overnight (the pH of the solution was measured to be 5-6). The impurities were extracted with a solution of 4/1 DCM/isopropanol (3×30 mL). The aqueous layer was then basified with NaOH solution (2 N) to a pH of about 9, and the pyridine was extracted with a solution of 4/1 DCM/isopropanol (3×30 mL). The aqueous solution was then acidified to a pH of about 2 and the product was extracted with a solution of 3/1 DCM/isopropanol (3×50 mL). The combined organic extracts were dried over MgSO$_4$, and the solvent was evaporated to afforded the pure product as a light brown solid in 90% yield. $^1$H NMR (DMSO-d$_6$): δ 13.80 (bs, 1H), 7.75 (d, 1H), 7.40 (d, 1H). IR (neat): (cm$^{-1}$) 3200, 2250, 1053, 1025, 1006.

B. 4-(4-Methyl-piperidin-1-yl)-3-nitro-phenyl]-methanol

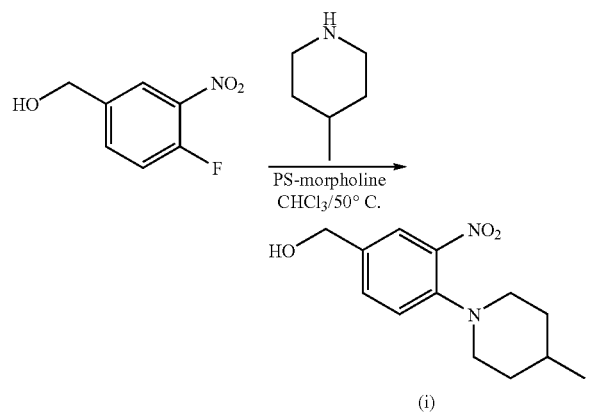

A stirred suspension of (4-fluoro-3-nitro-phenyl)-methanol (171 mg, 1 mmol), 4-methyl piperidine (95 mg, 0.96 mmol) PS morpholine (400 mg, 1 mmol), and chloroform (3 mL) was heated at 50° C. for 2 hrs. The reaction was evaporated onto celite and purified by flash chromatography to give [4-(4-methyl-piperidin-1-yl)-3-nitro-phenyl]-methanol (i). $^1$H NMR (CDCl$_3$, 300 MHz): δ 7.8 (s, 1H), 7.4 (d, 1H), 7.1 (d, 1H), 4.6 (s, 2H), 3.2 (d, 2H), 2.8 (dd, 2H), 1.8-1.3 (m, 5H), 1.0 (d, 3H).

C. 5-Cyano-furan-2-carboxylic acid [5-hydroxymethyl-2-(4-methyl-piperidin-1-yl)-phenyl]-amide

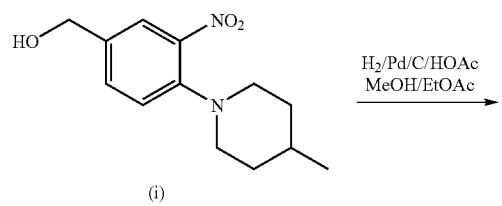

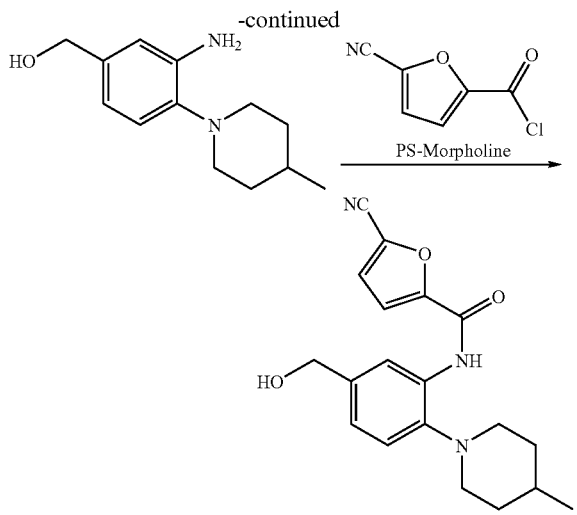

A suspension of 5% Pd/C (5.0 mg, 2.3×10$^{-3}$ mmol), [4-(4-methyl-piperidin-1-yl)-3-nitro-phenyl]-methanol (i) (95 mg, 0.38 mmol), acetic acid ("HOAc") (23 mg, 0.38 mmol), methanol (1 mL) and ethyl acetate (4 mL) was stirred in an atmosphere of hydrogen for 3 h. The reaction was filtered, concentrated in vacuo and the resulting [3-amino-4-(4-methyl-piperidin-1-yl)-phenyl]-methanol was used in the next step without further purification. A suspension of [3-amino-4-(4-methyl-piperidin-1-yl)-phenyl]-methanol, 5-cyano-2-furoyl chloride (64 mg, 0.44 mmol), PS morpholine (600 mg, 1.50 mmol), and DCM (10 mL) was stirred at room temperature for 30 min. The reaction was evaporated onto celite, and purified by column chromatography to give 5-cyano-furan-2-carboxylic acid [5-hydroxymethyl-2-(4-methyl-piperidin-1-yl)-phenyl]-amide. MS: 340 (M+1), $^1$H NMR (CDCl$_3$, 300 MHz): δ 9.9 (s br, 1H), 8.4 (s, 1H), 7.3 (s, 1H), 7.25-7.1 (m, 3H), 4.7 (s, 2H), 3.0 (m, 2H), 2.8 (m, 2H), 1.9, (d, 2H), 1.8-1.4 (m, 3H), 1.1 (d, 3H).

EXAMPLE 7

Procedure for Preparation of Biarylamides

5-Phenyl-furan-2-carboxylic acid (2-piperidin-1-yl-phenyl)-amide

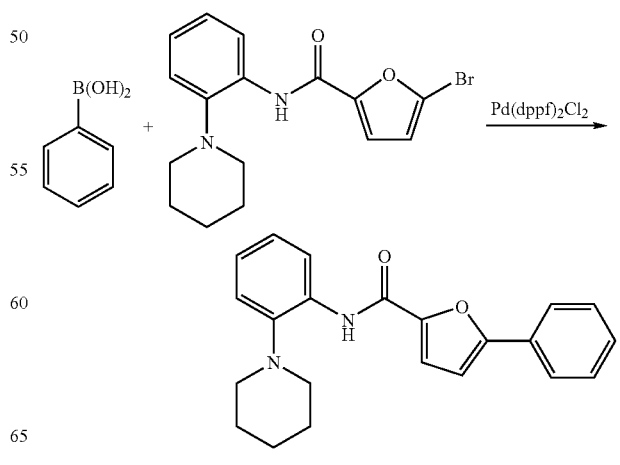

5-Bromo-furan-2-carboxylic acid (2-piperidin-1-yl-phenyl)-amide (1.0 mmol), phenylboronic acid (1.2 mmol), 1,1'-bis(diphenylphosphino)ferrocene]dichloropalladium (II) ["Pd(dppf)$_2$Cl$_2$"] (Aldrich) (0.05 mmol) and Na$_2$CO$_3$ (3.0 mmol) were dissolved in a solution of THF/H$_2$O (4:1, 5 mL; saturated with argon) and heated to 80° C. for 5 h. After cooling to room temperature, the mixture was concentrated under reduced pressure and the resulting residue was purified by silica gel chromatography to afford the pure product. Yield: 75%. MS: 347 (M+1). $^1$H NMR (CDCl$_3$, 300 MHz): δ 9.90 (br s, 1H), 8.50 (d, 1H), 7.82 (d, 2H), 7.50-7.28 (m, 4H), 7.24-7.05 (m, 3H), 6.82 (d, 1H), 3.00-2.80 (m, 4H), 1.95-1.80 (m, 4H), 1.75-1.60 (m, 2H).

EXAMPLE 8

Procedure for Extension of Aromatic Rings Through Amination

5-Phenylamino-furan-2-carboxylic acid (2-piperidin-1-yl-phenyl)-amide

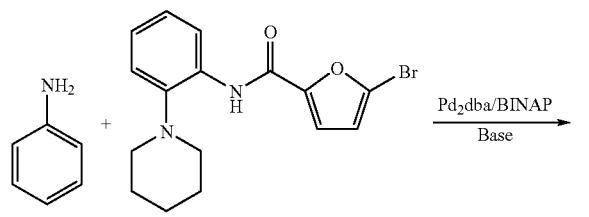

To a solution of 5-bromo-furan-2-carboxylic acid (2-piperidin-1-yl-phenyl)-amide (1.0 mmol) in toluene (7.5 mL) was added aniline (1.3 mmol), tris(dibenzylidineacetone)dipalladium(0) ("Pd$_2$dba") (Aldrich) (0.05 mmol), 2,2'-bis(diphenylphosphino)-1,1'-binaphthyl ("BINAP") (0.1 mmol), and potassium tert-butoxide ("t-BuOK") (1.5 mmol), and the resulting mixture was refluxed overnight. The reaction was then cooled to room temperature, passed through a plug of silica and concentrated. Purification of the dark brown residue by HPLC afforded the product. Yield: 40%. MS: 362 (M+1).

EXAMPLE 9

Procedure 1 for Preparation of the Compounds of Formula III

4-Oxo-6-piperidin-1-yl-4,5-dihydro-furo[2,3-c]guinoline-2-carbonitrile

5-Cyano-furan-2-carboxylic acid (2-piperidin-1-yl-phenyl)-amide (200 mg) is dissolved in a mixture of benzene (180 mL) and ethanol (20 mL). The solution is irradiated with a 100 W high pressure Hg Lamp at room temperature for 10 h, according to the method described by Kanoka and Itoh [*Synthesis*, 36 (1972)]. The solvent is removed in vacuo and the residue is purified by preparative thin layer chromatography ("TLC") (silica gel) to yield the pure product.

EXAMPLE 10

Procedure 2 for Preparation of the Compounds of Formula III

4-Oxo-6-piperidin-1-yl-4,5-dihydro-furo[2,3-c]quinoline-2-carbonitrile

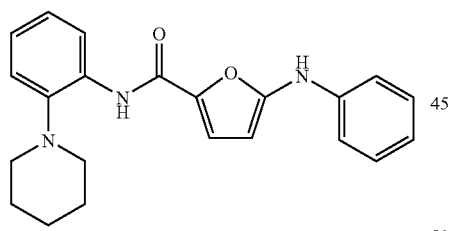

A solution of 2-nitro-3-bromotoluene (1.8 g, 8.3 mmol), piperidine (10 mL, 101 mmol), and dioxane (85 mL) was heated to reflux for 56 h. The reaction was filtered, concentrated and evaporated onto Celite. Chromatography on silica gel gave 1-(3-methyl-2-nitro-phenyl)-piperidine (i).

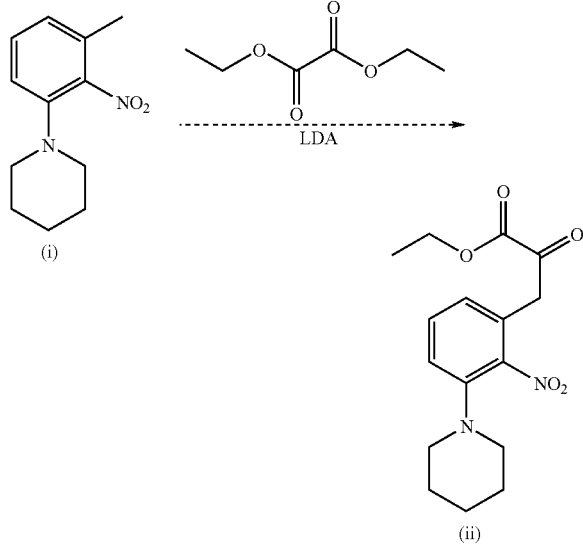

(i)

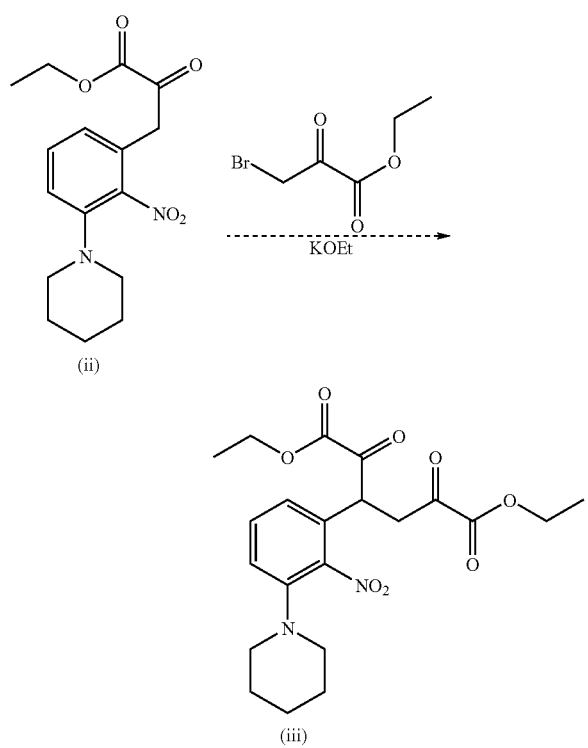

A solution of 1-(3-methyl-2-nitro-phenyl)-piperidine (i) in THF is treated with lithium diisopropylamide ("LDA") (1 eq), followed by diethyl oxalate (1.05 eq), at 0° C. The reaction is allowed to warm to room temperature over 90 min. The reaction is diluted with water and ether, partitioned, and the aqueous layer is washed with ether. The combined organic layers are dried over MgSO$_4$, filtered and concentrated. Chromatography gives 3-(2-nitro-3-piperidin-1-yl-phenyl)-2n-oxo-propionic acid ethyl ester (ii).

A solution of 3-(2-nitro-3-piperidin-1-yl-phenyl)-2-oxo-propionic acid ethyl ester (ii) in THF is treated with potassium ethoxide ("KOEt") (1 eq), followed by bromoethyl pyruvate (1.05 eq), at 0° C. The reaction is allowed to warm to room temperature over 90 min. The reaction is diluted with water and ether, partitioned, and the aqueous layer is washed with ether. The combined organic layers are dried over MgSO$_4$, filtered and concentrated. Chromatography gives 3-(2-nitro-3-piperidin-1-yl-phenyl)-2,5-dioxo-hexanedioic acid di ethyl ester (iii).

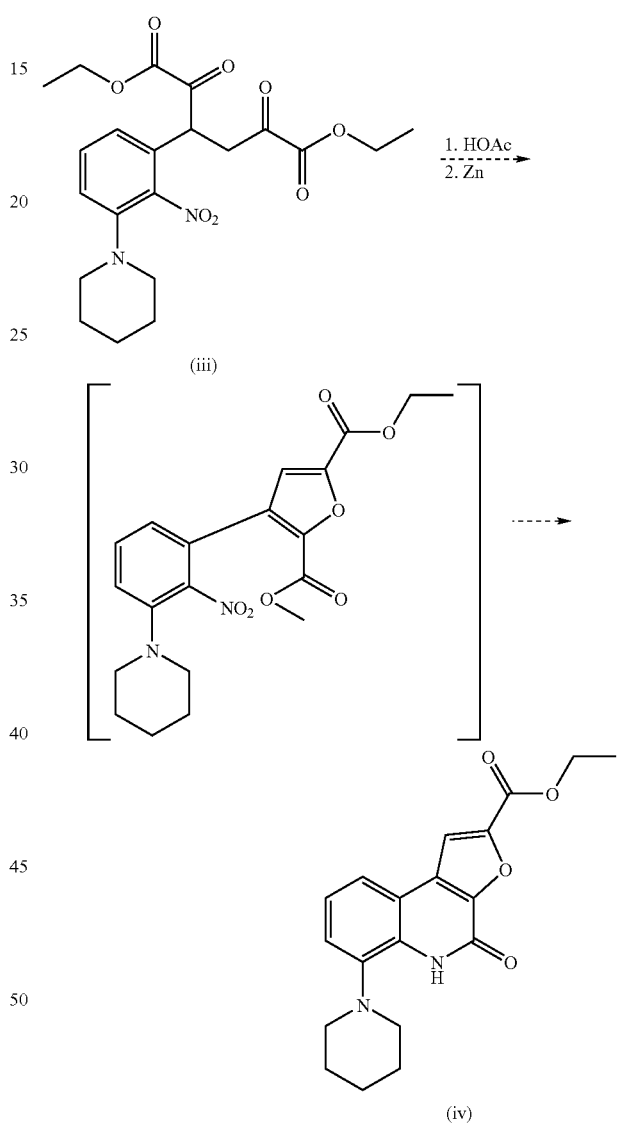

A solution of 3-(2-nitro-3-piperidin-1-yl-phenyl)-2,5-dioxo-hexanedioic acid diethyl ester (iii) in THF is treated with acetic acid ("HOAc") and is stirred at room temperature for 4 h. The reaction is treated with zinc dust (10 eq) and is stirred for an additional 2 h. The reaction is diluted with DCM, half saturated brine, and partitioned. The organic layer is washed with saturated aqueous NaHCO$_3$, dried over MgSO$_4$, filtered and concentrated. Chromatography gives 4-oxo-6-piperidin-1-yl-4,5-dihydro-furo[2,3-c]quinoline-2-carboxylic acid ethyl ester (iv).

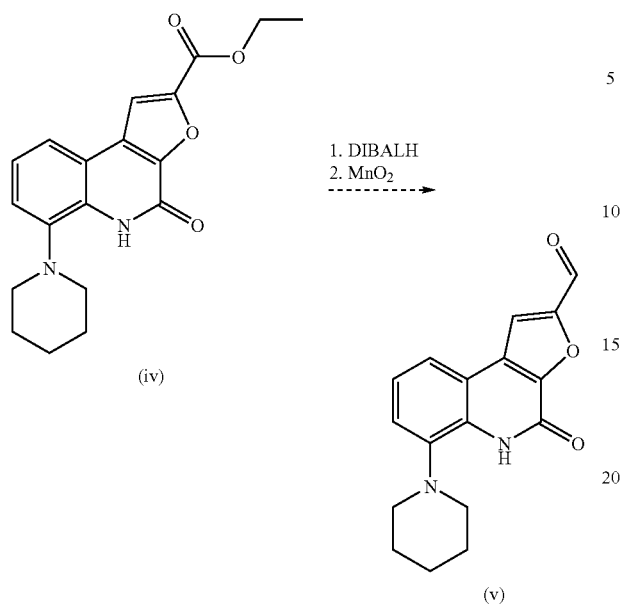

(iv)

1. DIBALH
2. MnO$_2$ (v)

A solution of 4-oxo-6-piperidin-1-yl-4,5-dihydro-furo[2,3-c]quinoline-2-carboxylic acid ethyl ester (iv) in DCM at 0° C. is treated with diisobutylaluminum hydride ("DIBAL-H") and is allowed to warm to room temperature. The reaction is quenched with a saturated solution of sodium potassium tartrate and partitioned. The organic layer is dried over MgSO$_4$, filtered and treated with manganese dioxide ("MnO$_2$"). After stirring for 16 h at room temperature, the reaction is filtered and is concentrated to give 4-oxo-6-piperidin-1-yl-4,5-dihydro-furo[2,3-c]quinoline-2-carbaldehyde (v).

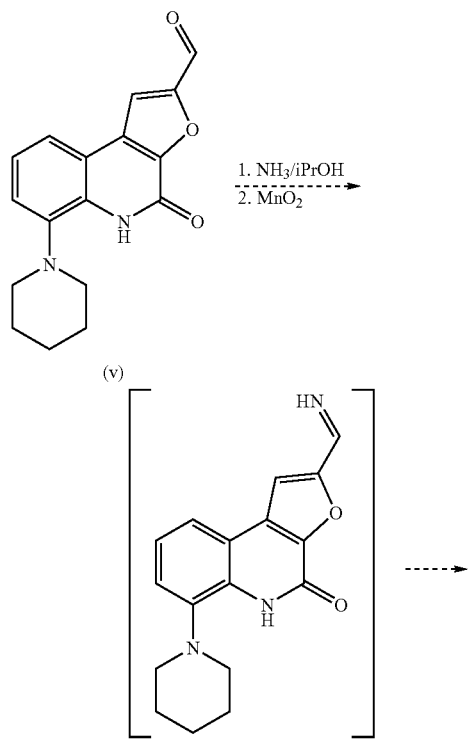

(v)

1. NH$_3$/iPrOH
2. MnO$_2$

-continued

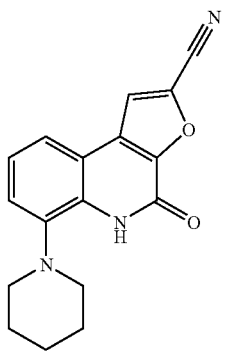

A solution of 4-oxo-6-piperidin-1-yl-4,5-dihydro-furo[2,3-c]quinoline-2-carbaldehyde (v) in isopropanol ("iPrOH") is treated with ammonia gas at room temperature. After 90 min, the reaction is treated with MnO$_2$ and stirred for an additional 16 h. The reaction is filtered and evaporated onto celite. Chromatography on silica gel affords 4-oxo-6-piperidin-1-yl-4,5-dihydro-furo[2,3-c]quinoline-2-carbonitrile.

IV. Results

An autophosphorylation, fluorescence polarization competition immunoassay was used to determine the potency for c-fms inhibition exhibited by selected compounds of Formulae I and II. The assay was performed in black 96-well microplates (LJL BioSystems). The assay buffer used was 100 mM HEPES, pH 7.5, 1 mM DTT, 0.01% (v/v) Tween-20. Compounds were diluted in assay buffer containing 4% DMSO just prior to the assay. To each well, 5 μL of compound were added followed by the addition of 3 μL of a mix containing 33 nM c-fms (3DP) and 16.7 mM MgCl$_2$ (Sigma) in assay buffer. The kinase reaction was initiated by adding 2 μL of 5 mM ATP (Sigma) in assay buffer. The final concentrations in the assay were 10 nM c-fms, 1 mM ATP, 5 mM MgCl$_2$, 2% DMSO. Control reactions were ran in each plate: in positive and negative control wells, assay buffer (made 4% in DMSO) was substituted for the compound; in addition, positive control wells received 1.2 μL of 50 mM EDTA.

The plates were incubated at room temperature for 45 min. At the end of the incubation, the reaction was quenched with 1.2 μL of 50 mM EDTA (EDTA was not added to the positive control wells at this point; see above). Following a 5-min incubation, each well received 10 μL of a 1:1:3 mixture of anti-phosphotyrosine antibody, 10×, PTK green tracer, 10× (vortexed), FP dilution buffer, respectively (all from PanVera, cat. # P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. The reported IC$_{50}$ values are averages of three independent measurements.

Table 1 lists representative compounds of Formulae I and II of the invention.

TABLE 1

| COMPOUND | IC$_{50}$ (uM) | % Inhibition (at 10 μM) |
| --- | --- | --- |
|  | A | 100 |
|  | A | 100 |
|  | A | 97 |
|  | A | 99 |
|  | A | 99 |
|  | A | 100 |

TABLE 1-continued

| COMPOUND | IC$_{50}$ (uM) | % Inhibition (at 10 μM) |
|---|---|---|
| [2-fluoro-6-piperidinyl-phenyl 5-cyano-furan-2-carboxamide] | B | 61 |
| [2-(4-methylpiperidin-1-yl)phenyl 5-nitro-furan-2-carboxamide] | A | 92 |
| [2-(4-hydroxymethylpiperidin-1-yl)phenyl 5-nitro-furan-2-carboxamide] | A | 100 |
| [2-(4-hydroxypiperidin-1-yl)phenyl 5-nitro-furan-2-carboxamide] | A | 98 |
| [2-(azepan-1-yl)phenyl 5-nitro-furan-2-carboxamide] | A | 100 |
| [2-piperidin-1-yl-phenyl 5-nitro-furan-2-carboxamide] | A | 91 |

TABLE 1-continued
| COMPOUND | IC$_{50}$ (uM) | % Inhibition (at 10 μM) |
|---|---|---|
| 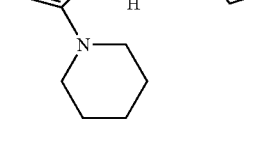 | A | 89 |
| 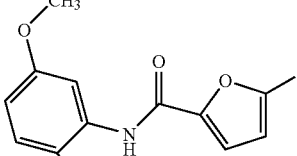 | A | 99* |
| 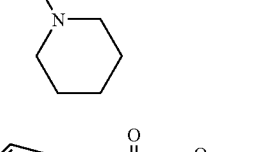 | A | 96 |
| 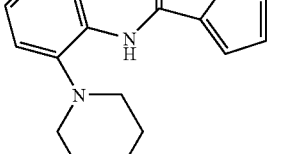 | B | 50 |
| 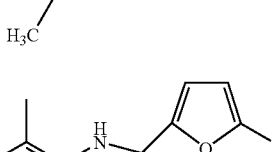 | A | 100 |
| 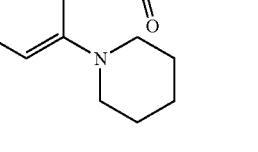 | B | 90 |

TABLE 1-continued

| COMPOUND | IC$_{50}$ (uM) | % Inhibition (at 10 μM) |
|---|---|---|
| 2-morpholinophenyl 5-nitrofuran-2-carboxamide | B | 89 |
| 2-piperidinophenyl 5-chlorofuran-2-carboxamide | B | 88 |
| 2-(chlorofluoromethyl-difluoromethylthio)phenyl 5-nitrofuran-2-carboxamide | B | 87 |
| 2-((2S,6R)-2,6-dimethylmorpholino)phenyl 5-nitrofuran-2-carboxamide | B | 80 |
| 2-piperidinophenyl 3-nitrobenzamide | B | 77 |
| 2-piperidinophenyl 5-bromofuran-2-carboxamide | B | 68 |
| 2-piperidinophenyl 5-acetylthiophene-2-carboxamide | B | 60 |

TABLE 1-continued

| COMPOUND | IC$_{50}$ (uM) | % Inhibition (at 10 μM) |
|---|---|---|
| | B | 72 |
| | B | 61 |
| | B | 56 |
| | B | 24 |
| | B | 86 |
| | B | 90* |

TABLE 1-continued
| COMPOUND | IC$_{50}$ (uM) | % Inhibition (at 10 μM) |
|---|---|---|
| 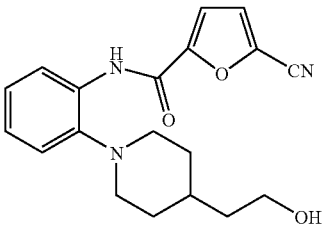 | A | 97* |
| 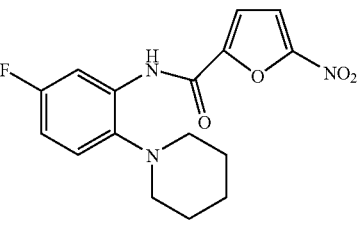 | A | ND |
| 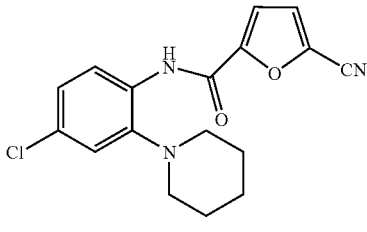 | A | 90* |
| 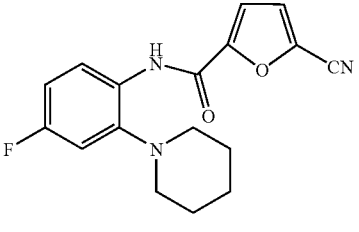 | A | 94* |
| 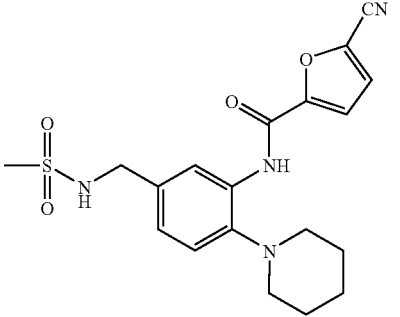 | A | 100* |

TABLE 1-continued

| COMPOUND | IC$_{50}$ (uM) | % Inhibition (at 10 μM) |
|---|---|---|
| (structure) | A | 94* |
| (structure) | A | 93* |
| (structure) | A | 95* |
| (structure) | B | 50* |

TABLE 1-continued

| COMPOUND | IC$_{50}$ (uM) | % Inhibition (at 10 μM) |
|---|---|---|
| 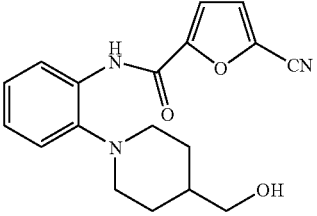 | A | 93* |

A: <1 μM
B: >1 μM
*= % Inhibition @ 2 μM
ND: not determined

The invention claimed is:

1. A compound of Formula I:

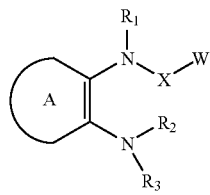

I or a solvate, hydrate, tautomer or pharmaceutically acceptable salt thereof, wherein A is phenyl, which may be optionally substituted with one or more of —C$_{1-6}$ alkyl, amino, aminoalkyl, hydroxyalkyl, alkoxyalkyl, sulfonamidoalkyl, guanidinoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —C(NH)NH$_2$, COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$;

R$_1$ is —H;

X is —CO—, or —CS—;

R$_2$ and R$_3$, taken together with the attached nitrogen, form a piperidine, or pyrrolidine ring which may be optionally substituted with —C$_{1-6}$ alkyl, amino, aminoalkyl, hydroxyalkyl, alkoxyalkyl, heteroaryl, halogen, hydroxy, —CF$_3$, alkoxy, aryl, aralkyl, heteroaralkyl, aryloxy, arylalkoxy, —OCF$_3$, —OCO-alkyl, —OCO-alkylamino, —OCO-alkylamido, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$, and wherein R$_a$ and R$_b$ are independently hydrogen, alkyl, cycloalkyl, haloalkyl, aryl, aralkyl, heteroaralkyl or heteroaryl;

and

W is furyl optionally substituted with —C$_{1-6}$ alkyl, amino, aminoalkyl, hydroxyalkyl, alkoxyalkyl, heteroaryl, halogen, hydroxy, —CF$_3$, alkoxy, aryl, aralkyl, heteroaralkyl, aryloxy, arylalkoxy, —OCF$_3$, —OCO-alkyl, —OCO-alkylamino, —OCO-alkylamido, —COR$_a$, —CN, —C(NH)NH$_2$, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$.

2. A compound of claim 1, which is one of 5-nitro-furan-2-carboxylic acid (2-piperidin-1-yl-phenyl)-amide;
5-nitro-furan-2-carboxylic acid (5-hydroxymethyl-2-piperidin-1-yl-phenyl)-amide;
5-nitro-furan-2-carboxylic acid [2-(3-methyl-piperidin-1-yl)-phenyl]-amide;
5-chloro-furan-2-carboxylic acid (2-piperidin-1-yl-phenyl)-amide;
5-bromo-furan-2-carboxylic acid (2-piperidin-1-yl-phenyl)-amide;
5-formyl-furan-2-carboxylic acid (2-piperidin-1-yl-phenyl)-amide;
5-cyano-furan-2-carboxylic acid (2-piperidin-1-yl-phenyl)-amide;
5-nitro-furan-2-carboxylic acid [2-(4-methyl-piperidin-1-yl)-phenyl]-amide;
5-nitro-furan-2-carboxylic acid [2-(4-hydroxy-piperidin-1-yl)-phenyl]-amide;
5-nitro-furan-2-carboxylic acid [2-(4-hydroxymethyl-piperidin-1-yl)-phenyl]-amide;
5-cyano-furan-2-carboxylic acid (5-hydroxymethyl-2-piperidin-1-yl-phenyl)-amide;
5-cyano-furan-2-carboxylic acid [2-(4-methyl-piperidin-1-yl)-phenyl]-amide;
5-cyano-furan-2-carboxylic acid [2-(4-hydroxymethyl-piperidin-1-yl)-phenyl]-amide;
5-cyano-furan-2-carboxylic acid {2-[4-(2-hydroxy-ethyl)-piperidin-1-yl]-phenyl}-amide;
5-cyano-furan-2-carboxylic acid [5-hydroxymethyl-2-(4-methyl-piperidin-1-yl)-phenyl]-amide;
5-cyano-furan-2-carboxylic acid [5-hydroxymethyl-2-(4-hydroxymethyl-piperidin-1-yl)-phenyl]-amide;
5-cyano-furan-2-carboxylic acid [2-(4-ethyl-piperidin-1-yl)-5-hydroxymethyl-phenyl]-amide;
5-cyano-furan-2-carboxylic acid {2-[4-(2-hydroxy-ethyl)-piperidin-1-yl]-5-hydroxymnethyl-phenyl}-amide;
5-cyano-furan-2-carboxylic acid [2-(4-ethyl-piperidin-1-yl)-phenyl]-amide;
5-cyano-furan-2-carboxylic acid (5-methylsulfonamidomethyl-2-piperidin-1-yl-phenyl)-amide;
5-cyano-furan-2-carboxylic acid (5-guanidinomethyl-2-piperidin-1-yl-phenyl)-amide;
5-cyano-furan-2-carboxylic acid (4-fluoro-2-piperidin-1-yl-phenyl)-amide;
5-cyano-furan-2-carboxylic acid (4-chloro-2-piperidin-1-yl-phenyl)-amide;
5-cyano-furan-2-carboxylic acid (5-cyano-2-piperidin-1-yl-phenyl)-amide; and
5-cyano-furan-2-carboxylic acid {5-[(2,3-dihydroxy-propylamino)-methyl]-2-piperidin-1-yl-phenyl}-amide.

* * * * *